(12) United States Patent
Matsui et al.

(10) Patent No.: US 8,512,985 B2
(45) Date of Patent: *Aug. 20, 2013

(54) SIGNAL PEPTIDE FOR PRODUCING A POLYPEPTIDE

(75) Inventors: Tomoko Matsui, Chiba (JP); Henriette Draborg, Alleroed (DK); Steffen Danielsen, Copenhagen O (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/357,223

(22) Filed: Jan. 24, 2012

(65) Prior Publication Data

US 2012/0122157 A1 May 17, 2012

Related U.S. Application Data

(63) Continuation of application No. 12/415,174, filed on Mar. 31, 2009, now Pat. No. 8,124,379, which is a continuation of application No. 11/152,811, filed on Jun. 14, 2005, now Pat. No. 7,527,947.

(60) Provisional application No. 60/580,151, filed on Jun. 16, 2004.

(30) Foreign Application Priority Data

Jun. 14, 2004 (DK) .................................. 2004 00917

(51) Int. Cl.
*C12N 15/62* (2006.01)
*C12N 15/80* (2006.01)
*C12N 15/81* (2006.01)

(52) U.S. Cl.
USPC .................. 435/69.7; 435/254.11; 435/254.2; 435/254.3; 435/320.1; 536/23.4

(58) Field of Classification Search
None
See application file for complete search history.

(56) References Cited

U.S. PATENT DOCUMENTS

| 5,639,642 | A | 6/1997 | Kieldsen |
| 5,827,719 | A | 10/1998 | Sandal |
| 6,004,776 | A | 12/1999 | Guiseppin |
| 6,495,357 | B1 | 12/2002 | Fuglsang |
| 7,173,117 | B2 | 2/2007 | Bollen |
| 7,527,947 | B2 * | 5/2009 | Matsui et al. ................. 435/69.8 |
| 8,124,379 | B2 * | 2/2012 | Matsui et al. ................. 435/69.7 |
| 2003/0082595 | A1 | 5/2003 | Jiang |
| 2005/0069978 | A1 * | 3/2005 | Bower et al. ................. 435/69.1 |

FOREIGN PATENT DOCUMENTS

| EP | 1375664 A1 | 2/2004 |
| WO | 9613580 A1 | 5/1996 |
| WO | 0210414 A2 | 2/2002 |
| WO | 03004636 A2 | 1/2003 |

OTHER PUBLICATIONS

Carvalho et al., Cutinase Structure, Function and Biocatalytic Applications, Journal of Biotechnology, vol. 1, part 3, pp. 161-173 (1998).

* cited by examiner

*Primary Examiner* — Manjunath Rao
*Assistant Examiner* — William W Moore
(74) *Attorney, Agent, or Firm* — Michael W. Krenicky; Robert L. Starnes

(57) ABSTRACT

The present invention relates to a method for producing a polypeptide comprising using a signal peptide, to nucleic acid constructs comprising a first nucleotide sequence encoding the signal peptide and a second nucleotide sequence encoding a polypeptide which is foreign to the first nucleotide sequence. Furthermore, it also relates to expression vectors and host cells comprising the nuclei acid construct.

15 Claims, No Drawings

SIGNAL PEPTIDE FOR PRODUCING A POLYPEPTIDE

CROSS-REFERENCE TO RELATED APPLICATIONS

This application is a continuation of U.S. application Ser. No. 12/415,174 filed Mar. 31, 2009 (now U.S. Pat. No. 8,124, 379), which is a continuation of U.S. application Ser. No. 11/152,811 filed Jun. 14, 2005 (now U.S. Pat. No. 7,527,947), which claims priority or the benefit under 35 U.S.C. 119 of Danish Application no. PA 2004 00917 filed Jun. 14, 2004 and U.S. provisional application No. 60/580,151 filed Jun. 16, 2004, the contents of which are fully incorporated herein by reference.

REFERENCE TO SEQUENCE LISTING

The present application contains information in the form of a sequence listing, which is appended to the application and also submitted on a data carrier accompanying this application. The content of the data carrier is fully incorporated herein by reference.

FIELD OF THE INVENTION

The present invention relates to methods for producing a polypeptide comprising using a signal peptide foreign to the polypeptide, nucleic acid constructs comprising a first and a second nucleotide sequence encoding the signal peptide and the polypeptide and expression vectors and host cells comprising said nucleic acid construct.

BACKGROUND OF THE INVENTION

The recombinant production of a heterologous protein in a fungal host cell, particularly a filamentous fungal cell such as *Aspergillus* or a yeast cell such *Saccharomyces*, may provide for a more desirable vehicle for producing the protein in commercially relevant quantities.

Recombinant production of a heterologous protein is generally accomplished by constructing an expression cassette in which the DNA coding for the protein is placed under the expression control of a promoter, excised from a regulated gene, suitable for the host cell. The expression cassette is introduced into the host cell. Production of the heterologous protein is then achieved by culturing the transformed host cell under inducing conditions necessary for the proper functioning of the promoter contained on the expression cassette.

Improvement of the recombinant production of proteins generally requires the availability of new regulatory sequences which are suitable for controlling the expression of the proteins in a host cell.

It is an object of the present invention to provide improved methods for producing a polypeptide in a fungal host cell using signal peptide sequences.

SUMMARY OF THE INVENTION

The invention provides a method for producing a secreted polypeptide, comprising:
 (a) cultivating an fungal host cell in a medium conducive for the production of the polypeptide, wherein the host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence, the 3' end of the first nucleotide sequence is immediately upstream of the second nucleotide sequence, and the first nucleotide sequence is selected from the group consisting of:
  (i) a nucleotide sequence encoding a signal peptide having an amino acid sequence which has at least 70% identity with SEQ ID NO:1;
  (ii) a nucleotide sequence having at least 70% homology with SEQ ID NO: 2; and
  (iii) a nucleotide sequence which hybridizes under stringency conditions with the nucleotides of SEQ ID NO: 2, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm; and
 (b) isolating the secreted polypeptide from the cultivation medium.

Furthermore, the present invention provides for A nucleic acid construct comprising a first nucleotide sequence encoding a signal peptide operably linked to a second nucleotide sequence encoding a polypeptide, wherein the first nucleotide sequence is foreign to the second nucleotide sequence, and the 3' end of the first nucleotide sequence is immediately upstream of the second nucleotide sequence, and the first nucleotide sequence is selected from the group consisting of:
 (a) a nucleotide sequence encoding a signal peptide having an amino acid sequence which has at least 70% identity with SEQ ID NO:1;
 (b) a nucleotide sequence having at least 70% homology with SEQ ID NO: 2; and
 (c) a nucleotide sequence which hybridizes under stringency conditions with the nucleotides of SEQ ID NO: 2, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm.

The present invention also provides expression vectors and host cells comprising said nucleic acid construct.

DETAILED DESCRIPTION OF THE INVENTION

Definitions

The term "variant" when used in reference to another polypeptide or nucleotide sequence is in the context of the present invention to be understood as a polypeptide or nucleotide sequence which comprises a substitution, deletion, and/or insertion of one or more amino acids or nucleotides as compared to another polypeptide (i.e. it is a variant of polypeptide/nucleotide sequence it is compared with). In particular the changes may be of minor nature, such as conservative amino acid substitutions or for nucleotide sequence resulting in conservative amino acid substitutions, that do not significantly affect the activity of the polypeptide; or small deletions, typically of one to about 20 amino acids depending on the size of the polypeptide in which the changes are made.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Method of the Present Invention

The present invention relates to methods for producing a secreted polypeptide, comprising: (a) cultivating a fungal host cell in a medium conducive for the production of the polypeptide, wherein the host cell comprises a nucleic acid construct comprising a first nucleotide sequence encoding a signal peptide operably linked to a second nucleotide sequence encoding the polypeptide, wherein the first nucleotide sequence is foreign to the second nucleotide sequence, the 3' end of the first nucleotide sequence is immediately upstream of the second nucleotide sequence, and the first nucleotide sequence is selected from the group consisting of: (i) a nucleotide sequence encoding a signal peptide having an amino acid sequence which has at least 70% identity with SEQ ID NO:1; (ii) a nucleotide sequence having at least 70% homology with SEQ ID NO: 2; and (iii) a nucleotide sequence which hybridizes under stringency conditions with the nucleotides of SEQ ID NO: 2, or its complementary strand, wherein the stringency conditions are defined as prehybridization, hybridization, and washing post-hybridization at 5° C. to 10° C. below the calculated Tm in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml, and washing once in 6×SCC plus 0.1% SDS for 15 minutes and twice each for 15 minutes using 6×SSC at 5° C. to 10° C. below the calculated Tm; and (b) isolating the secreted polypeptide from the cultivation medium.

In the methods of the present invention, the fungal host cells are cultivated in a medium conducive for the production of the polypeptide, i.e. in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation may take place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

The polypeptide may be detected using methods known in the art that are specific for the polypeptide. Such detection methods may include use of specific antibodies, formation of an enzyme product, or disappearance of an enzyme substrate.

In the methods of the present invention, the fungal host cell may in particular produce at least about 25% more, more particularly at least about 50% more, more particularly at least about 75% more, more particularly at least about 100% more, even more particularly at least about 200% more, most particularly at least about 300% more, and even most particularly at least about 400% more polypeptide relative to a fungal cell containing a native signal peptide sequence operably linked to a nucleotide sequence encoding the polypeptide when cultured under identical production conditions.

The resulting secreted polypeptide can be recovered directly from the medium by methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Signal Peptide

The first nucleotide sequence of the present encodes a signal peptide of the present invention. The term "signal peptide" or "signal peptide sequence" is defined herein as a peptide sequence usually present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed. In particular said signal peptide may be capable of directing the polypeptide into a cell's secretory pathway.

The term "operably linked" is defined herein as a configuration in which a control sequence, e.g., a signal peptide sequence, is appropriately placed at a position relative to a coding sequence such that the control sequence directs the production of a polypeptide encoded by the coding sequence.

The term "coding sequence" is defined herein as a nucleotide sequence which is translated into a polypeptide when placed under the control of the appropriate control sequences. The boundaries of the coding sequence are generally determined by the start codon located at the beginning (5' end) of the open reading frame and a stop codon located at the 3' end of the open reading frame. A coding sequence can include, but is not limited to, genomic DNA, cDNA, RNA, semisynthetic, synthetic, and recombinant nucleotide sequences.

The 5' end of the coding sequence of the polypeptide of the present invention may contain a native nucleotide sequence encoding a signal peptide which is naturally linked with nucleotide sequence segment which encodes the mature (or pro-form) of the polypeptide. In this case the signal peptide of the present invention may replace the native signal peptide. Alternatively, the polypeptide of the present invention may lack a native signal peptide. In this context the term "native" is intended to be understood as being present naturally.

In the methods of the present invention, the signal peptide sequence is foreign to the nucleotide sequence encoding a polypeptide of interest, but the signal peptide sequence or nucleotide sequence may be native to the fungal host cell. In this context the term "foreign" is intended to be understood as the signal peptide is not native to the polypeptide, i.e. it originates from another gene than the polypeptide.

In one embodiment the first nucleotide sequence may encode a signal peptide having an amino acid sequence which has at least 70%, particularly at least about 75%, more particularly at least about 80%, more particularly at least about 85%, even more particularly at least about 90%, most particularly at least about 95%, and even most particularly at least about 97% identity to SEQ ID NO: 1, which have the ability to direct a polypeptide into or across a cell membrane (hereinafter "homologous signal peptide"), e.g. into a cell's secretory pathway. In a particular aspect, the homologous signal peptide may have an amino acid sequence which differs by five amino acids, particularly by four amino acids, more particularly by three amino acids, even more particularly by two amino acids, and most particularly by one amino acid from SEQ ID NO: 1. For purposes of the present invention, the identity or degree of identity between two amino acid sequences is determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

In particular, the first nucleotide sequence may encode a signal peptide which comprises the amino acid sequence of SEQ ID NO: 1, or an allelic variant thereof; or a fragment thereof that has the ability to direct the polypeptide into or across a cell membrane, e.g. into a cell's secretory pathway. In a more particular aspect, the first nucleotide sequence of the present invention encodes a signal peptide that comprises the amino acid sequence of SEQ ID NO: 1. In another particular aspect, the first nucleotide sequence encodes a signal peptide that consists of the amino acid sequence of SEQ ID NO: 1, or a fragment thereof, wherein the signal peptide fragment has the ability to direct a polypeptide into or across a cell membrane, e.g. into a cell's secretory pathway. In another more particular aspect, the nucleotide sequence of the present invention encodes a signal peptide that consists of the amino acid sequence of SEQ ID NO: 1.

The present invention also encompasses first nucleotide sequences which encode a signal peptide having the amino acid sequence of SEQ ID NO: 1, which differs from SEQ ID NO: 2 by virtue of the degeneracy of the genetic code. The present invention also relates to subsequences or fragments of SEQ ID NO: 2 which encode fragments of SEQ ID NO: 1 which has the ability to direct a polypeptide into or across a cell membrane, e.g. into a cell's secretory pathway.

A subsequence of SEQ ID NO: 2 is a nucleic acid sequence encompassed by SEQ ID NO: 2 except that one or more nucleotides from the 5' and/or 3' end have been deleted. Particularly, a subsequence contains at least 30 nucleotides, such as at least 35 nucleotides or at least 40 nucleotides or at least 45 nucleotides or at least 50 nucleotides or at least 52 nucleotides or at least 53 nucleotides. A fragment of SEQ ID NO: 1 is a polypeptide having one or more amino acids deleted from the amino and/or carboxy terminus of this amino acid sequence. In particular a fragment contains at least 10 amino acid residues. such as at least 12 amino acid residues or at least 13 amino acid residues or at least 14 amino acid residues or at least 15 amino acid residues or at least 16 amino residues or at least 17 amino acid residues. In particular if the first and second nucleotide sequences are expressed in a yeast host cell the signal peptide may comprise amino acid residues 1-16 of SEQ ID NO: 1, as the inventors of the present invention have observed that in yeast the signal peptide is cleaved between amino acid residues 16 and 17 (at the AAP), while if the host cell is a filamentous fungus the signal peptide may in particular comprise the 18 amino acid residues of SEQ ID NO: 1, as the inventors of the present invention have seen that in *Aspergillus oryzae* the cleavage of the signal peptide occurs after amino acid residue 18 of SEQ ID NO:1. This indicates that there may be a difference between yeast and filamentous fungi in the sequence recognized as a cleavage site for cleavage of the signal sequence.

An allelic variant denotes any of two or more alternative forms of a gene occupying the same chromosomal locus. Allelic variation arises naturally through mutation, and may result in polymorphism within populations. Gene mutations may be silent (no change in the encoded signal peptide) or may encode signal peptides having altered amino acid sequences. The allelic variant of a signal peptide is a peptide encoded by an allelic variant of a gene.

In a particular aspect, the first nucleotide sequence is the signal peptide coding sequence of the cutinase gene contained in *Humicola insolens* DSM 1800 (SEQ ID NO: 1).

In a second aspect, the first nucleotide sequence of the present invention which encodes a signal peptide may have a degree of homology to SEQ ID NO: 2 of at least about 70%, particularly at least about 75%, more particularly at least about 80%, more particularly at least about 85%, even more particularly at least about 90% homology, most particularly at least about 95% homology, and even most particularly at least about 97% homology, which encode a signal peptide; or allelic variants and subsequences of SEQ ID NO: 2 which encode signal peptide fragments which have the ability to direct a polypeptide into or across a cell membrane, e.g. into a cell's secretory pathway. For purposes of the present invention, the degree of homology between two nucleic acid sequences is determined by the Wilbur-Lipman method (Wilbur and Lipman, 1983, Proceedings of the National Academy of Science USA 80: 726-730) using the LASERGENET™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

In a third aspect, the first nucleotide sequence of the present invention encodes a signal peptide, wherein said first nucleotide sequence hybridize under stringency conditions with the nucleotides of SEQ ID NO: 2, or its complementary strand (J. Sambrook, E. F. Fritsch, and T. Maniatus, 1989, Molecular Cloning, A Laboratory Manual, 2d edition, Cold Spring Harbor, N.Y.).

The nucleotide sequence of SEQ ID NO: 2 or a subsequence thereof, as well as the amino acid sequence of SEQ ID NO: 1 or a fragment thereof may be used to design a nucleic acid probe to identify and clone DNA encoding signal peptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but may in particular be at least 15, such as at least 25, or more particularly at least 35 nucleotides in length. Both DNA and RNA probes can be used. The probes may typically be labelled for detecting the corresponding gene (for example, with $^{32}P$, 3H, $^{35}S$, biotin, or avidin). Such probes are encompassed by the present invention.

Thus, a genomic DNA or cDNA library prepared from such other organisms may be screened for DNA which hybridizes with the probes described above and which encodes a signal peptide. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 2 or a subsequence thereof, the carrier material is used in a Southern blot. For purposes of the present invention, hybridization indicates that the nucleic acid sequence hybridizes to a labelled nucleic acid probe corresponding to the nucleic acid sequence shown in SEQ ID NO: 2, its complementary strand, or a subsequence thereof, under stringency conditions defined herein. Molecules to which the nucleic acid probe hybridizes under these conditions can be detected using X-ray film.

In a particular aspect, the nucleic acid probe is a nucleotide sequence which encodes the signal peptide of SEQ ID NO: 1, or a subsequence thereof. In another particular aspect, the nucleic acid probe is SEQ ID NO: 2. In another particular aspect, the nucleic acid probe is the signal peptide sequence of the cutinase gene contained in *Humicola insolens* DSM 1800 (SEQ ID NO: 2 of WO 96/13580).

For short probes which are about 15 nucleotides to about 60 nucleotides in length, stringency conditions are defined as prehybridization, hybridization, and washing post-hybridization at 5° C. to 10° C. below the calculated Tm using the calculation according to Bolton and McCarthy (1962, Proceedings of the National Academy of Sciences USA 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 60 nucleotides in length, the carrier material is washed once in 6×SCC plus 0.1% SDS for 15 minutes and twice each for 15 minutes using 6×SSC at 5° C. to 10° C. below the calculated Tm.

In a fourth aspect, the first nucleotide sequence may encode variants of the signal peptide having an amino acid sequence of SEQ ID NO: 1 comprising a substitution, deletion, and/or insertion of one or more amino acids.

The amino acid sequences of the variant signal peptides may differ from the amino acid sequence of SEQ ID NO: 1 by an insertion or deletion of one or more amino acid residues and/or the substitution of one or more amino acid residues by different amino acid residues. Particularly, amino acid changes may be of a minor nature, such as conservative amino acid substitutions that do not significantly affect the activity of the signal peptide; or small deletions, typically of one to about 5 amino acids.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Polypeptide

The second nucleotide sequence of the preset invention encodes a polypeptide encoded of the present invention. Said polypeptide may be native or heterologous to the fungal host cell in which it is produced.

The term "polypeptide" is not meant herein to refer to a specific length of the encoded product and, therefore, encompasses peptides, oligopeptides, and proteins. The term "heterologous polypeptide" is defined herein as a polypeptide which is not native to the fungal cell, a native polypeptide in which modifications have been made to alter the native sequence, or a native polypeptide whose expression is quantitatively altered as a result of a manipulation of the gene encoding the polypeptide by recombinant DNA techniques. The fungal cell may contain one or more copies of the nucleotide sequence encoding the polypeptide.

In particular, the polypeptide may be a hormone or hormone variant, an enzyme, a receptor or portion thereof, an antibody or portion thereof, an allergen or a reporter. In a particular aspect, the polypeptide may be an allergen originating from *Dermatophagoides pteronyssinus, Dermatophagoides farinae, Dermatophagoides siboney, Dermatophagoides microceaus, Blomia tropicalis* and *Euroglyphus maynei*, or an allergen from one of said organisms which subsequently have been modified. More particularly, said allergen may be Der p 1, e.g. Der p 1 from *Dermantophagoides pteronyssinus* (SEQ ID NO: 3). In particular the polypeptide may be the sequence of amino acids 19-320 of SEQ ID NO: 3. In a more particular embodiment the polypeptide may be a variant of the polypeptide sequence of amino acids 19-320 of SEQ ID NO: 3. More particularly said variant may be a S54X or N52X, wherein "X" denotes any amino acid, as said disrupt the N-glycosylation site of Der p 1, in particular said variants may be S54N or N52Q. However, other variants of Der p 1 are envisioned.

In another particular embodiment the polypeptide may be an enzyme, such as an oxidoreductase, transferase, hydrolase, lyase, isomerase, or ligase. In a more particular aspect, the polypeptide may be an aminopeptidase, amylase, carbohydrase, carboxypeptidase, catalase, cellulase, cellobiohydrolase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, or beta-xylosidase. An example of a relevant cellulase includes but is not limited to a cellulase from *Mucor cicinellides*, e.g. *M. cicinellides* IFO4554 (SEQ ID NO: 4). Examples of relevant proteolytic enzymes include but are not limited to cystein proteases, e.g. cystein protease 5 from *Trifolium repens* L (SEQ ID NO: 5), especially amino acids 109-327 of SEQ ID NO: 5 which encode the mature peptide, or trypsin, e.g. trypsin from *Fusarium oxysporium* (SEQ ID NO: 7). An example of a relevant phytase includes but is not limited to a phytase from *Peniophora lycii*, e.g. *P. lycii* CBS 686.96 (SEQ ID NO: 9).

The second nucleotide sequence encoding a polypeptide of the present invention may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleotide sequence encoding a polypeptide of interest are known in the art and include isolation from genomic DNA, preparation from cDNA, or a combination thereof. The cloning of the second nucleotide sequence from such genomic DNA can be effected, e.g., by using the well known polymerase chain reaction (PCR). See, for example, Innis et al., 1990, PCR Protocols: A Guide to Methods and Application, Academic Press, New York. The cloning procedures may involve excision and isolation of a desired nucleotide fragment comprising the nucleotide sequence encoding the polypeptide, insertion of the fragment into a vector molecule, and incorporation of the recombinant vector into the mutant fungal cell where multiple copies or clones of the nucleotide sequence will be replicated. The second nucleotide sequence may be of genomic, cDNA, RNA, semisynthetic, synthetic origin, or any combinations thereof.

In the methods of the present invention, the polypeptide may also be a fused or hybrid polypeptide in which another polypeptide is fused at the N-terminus or the C-terminus of the polypeptide or fragment thereof. A fused polypeptide is produced by fusing a nucleotide sequence (or a portion thereof) encoding one polypeptide to the second nucleotide sequence (or a portion thereof) encoding the polypeptide of the present invention. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the mutant fungal cell.

Nucleic Acid Construct

The present invention also relates to a nucleic acid construct comprising a first nucleotide sequence signal peptide of the present invention operably linked to a second nucleotide sequence encoding a polypeptide of the present invention.

"Nucleic acid construct" is defined herein as a nucleotide molecule, either single- or double-stranded, which is isolated from a naturally occurring gene or which has been modified to contain segments of nucleic acids combined and juxtaposed in a manner that would not otherwise exist in nature. The term nucleic acid construct is synonymous with the term expression cassette when the nucleic acid construct contains a coding sequence and all the control sequences required for expression of the coding sequence.

A second nucleotide sequence encoding a polypeptide may be further manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

In the methods of the present invention, the nucleic acid construct may comprise one or more native control sequences or one or more of the native control sequences may be replaced with one or more control sequences foreign to the first and/or second nucleotide sequence of the nucleic acid construct for improving expression of the second nucleotide sequence encoding a polypeptide in a host cell.

The term "control sequences" is defined herein to include all components which are necessary or advantageous for the expression of the polypeptide encoded by the second nucleotide sequence. Each control sequence may be native or foreign to the second nucleotide sequence encoding the polypeptide. Such control sequences include, but are not limited to, a leader, polyadenylation sequence, propeptide sequence, signal peptide sequence of the present invention, and transcription terminator. At a minimum, the control sequences include a signal peptide sequence of the present invention, and transcriptional and translational stop signals. The control sequences may be provided with linkers for the purpose of introducing specific restriction sites facilitating ligation of the control sequences with the second nucleotide sequence encoding the polypeptide.

The control sequence may be an appropriate promoter sequence, which is recognized by a host cell for expression of the nucleotide sequence. The promoter sequence contains transcriptional control sequences which mediate the expression of the polypeptide. The promoter may be any sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters include but are not limited to those obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may be a suitable transcription terminator sequence, which is recognized by a host cell to terminate transcription. The terminator sequence is operably linked to the 3' terminus of the nucleotide sequence encoding the polypeptide. Any terminator which is functional in the host cell of choice may be used in the present invention.

Examples of suitable terminators for filamentous fungal host cells include but are not limited to those obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Examples of suitable terminators for yeast host cells include but are not limited to those obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence may generally be operably linked to the 5' end of the nucleotide sequence encoding a polypeptide. Any leader sequence that is functional in the host cell of choice may be used in the present invention.

Examples of suitable leaders for filamentous fungal host cells include but are not limited to those obtained from the genes for *Aspergillus oryzae* TAKA amylase and *Aspergillus nidulans* triose phosphate isomerase.

Suitable leaders for yeast host cells include but are not limited to those obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, which is operably linked to the 3' end of the nucleotide sequence encoding a polypeptide and which, when transcribed, is recognized by the host cell as a signal to add polyadenosine residues to transcribed mRNA. Any polyadenylation sequence which is functional in the host cell of choice may be used in the present invention.

Examples of suitable polyadenylation sequences for filamentous fungal host cells include but are not limited to those obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells include but are not limited to those described by Guo and Sherman, 1995, Molecular Cellular Biology 15: 5983-5990.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. Examples of propeptide coding region include but are not limited to those obtained from the genes for *Dermantophagoides pteronyssinus* Der p 1, or other genes obtained from *Dermantophagoides*, *Fusarium oxysporum* trypsin, *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region. If a propeptide is present a cleavable site may in one embodiment be present between the propeptide and the mature polypeptide. The term "cleavable site" is to be understood as an amino acid sequence which is recognized by a proteolytic enzyme capable of cleaving the polypeptide at this site. Examples of such site include a kex-site, in particular a kex-II site.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vector

The present invention also relates to a recombinant expression vector comprising a nucleic acid construct of the present invention. Besides comprising a first and a second nucleotide sequence encoding a signal peptide and a polypeptide, respectively of the present invention said expression vector may in particular comprise a transcriptional and translational stop signal. The various nucleotide and control sequences described above may be joined together to produce a recombinant expression vector which may include one or more convenient restriction sites to allow for insertion or substitution of the promoter and/or nucleotide sequence encoding the polypeptide at such sites. Alternatively, the nucleic acid construct may be inserted into an appropriate vector for expression for expression of the polypeptide encoded by the second nucleotide sequence. In creating the expression vector, the second nucleotide sequence encoding the polypeptide of the present invention is located in the vector so that said sequence is operably linked with a signal peptide sequence of the present invention and one or more appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vectors of the present invention may in particular contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. In particular for use in an *Aspergillus* cell are the amdS and pyrG genes of *Aspergillus nidulans* or *Aspergillus oryzae* and the bar gene of *Streptomyces hygroscopicus*.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention may in particular contain an element(s) that permits stable integration of the vector into the host cell's genome or autonomous replication of the vector in the cell independent of the genome.

For integration into the host cell genome, the vector may rely on the second nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences may enable the vector to be integrated into the host cell genome at a precise location(s) in the chromosome(s). To increase the likelihood of integration at a precise location, the integrational elements should in particular contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its ability to function temperature-sensitive in the host cell (see, e.g., Ehrlich, 1978, Proceedings of the National Academy of Sciences USA 75: 1433).

Examples of origins of replication useful in a filamentous fungal host cell are AMA1 and ANS1 (Gems et al., 1991, Gene 98:61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a nucleotide sequence encoding a polypeptide may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention relates to methods in which polypeptides are produced in a fungal host cell and to a recombinant host cells comprising a nucleic acid construct of the present invention.

A vector comprising a first nucleotide sequence encoding a signal peptide of the present invention operably linked to a second nucleotide sequence encoding a polypeptide is introduced into a fungal host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a particular aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In a more particular aspect, the yeast host cell is a *Candida, Hansenula, Kluyveromyces, Pichia, Saccharomyces, Schizosaccharomyces,* or *Yarrowia* cell.

In a most particular aspect, the yeast host cell is a *Saccharomyces carlsbergensis, Saccharomyces cerevisiae,* e.g., *S. cerevisiae* YNG318, *Saccharomyces diastaticus, Saccharomyces douglasii, Saccharomyces kluyveri, Saccharomyces norbensis, Saccharomyces oviformis, Kluyveromyces lactis* or *Yarrowia lipolytica* cell.

In another particular aspect, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more particular aspect, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In an even more particular aspect, the filamentous fungal host cell is an *Aspergillus awamori, Aspergillus foetidus, Aspergillus japonicus, Aspergillus nidulans, Aspergillus niger* or *Aspergillus oryzae* cell. In another even more particular aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another even more particular aspect, the filamentous fungal host cell is a *Humicola insolens, Humicola*

*lanuginosa*, *Mucor miehei*, *Myceliophthora thermophila*, *Neurospora crassa*, *Penicillium purpurogenum*, *Thielavia terrestris*, *Trichoderma harzianum*, *Trichoderma koningii*, *Trichoderma longibrachiatum*, *Trichoderma reesei*, or *Trichoderma viride* cell.

In a most particular aspect, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, Fungal Genetics and Biology 23: 62-80 and O'Donnell et al., 1998, Fungal Genetics and Biology 23: 57-67; as well as taxonomic equivalents of *Fusarium venenatum* regardless of the species name by which they are currently known. In another particular aspect, the *Fusarium venenatum* cell is a morphological mutant of *Fusarium venenatum* A3/5 or *Fusarium venenatum* ATCC 20334, as disclosed in WO 97/26330.

In another most particular aspect, the *Trichoderma* cell is *Trichoderma reesei* ATCC 56765, *Trichoderma reesei* ATCC 13631, *Trichoderma reesei* CBS 526.94, *Trichoderma reesei* CBS 529.94, *Trichoderma longibrachiatum* CBS 528.94, *Trichoderma longibrachiatum* ATCC 2106, *Trichoderma longibrachiatum* CBS 592.94, *Trichoderma viride* NRRL 3652, *Trichoderma viride* CBS 517.94, or *Trichoderma viride* NIBH FERM/BP 447.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, Proceedings of the National Academy of Sciences USA 81: 1470-1474. Suitable procedures for transformation of *Trichoderma reesei* host cells are described in Penttila et al., 1987, Gene 61: 155-164, and Gruber et al., 1990, Curr Genet. 18(1):71-6. Suitable methods for transforming *Fusarium* species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology 194: 182-187, Academic Press, Inc., New York; Ito et al., 1983, Journal of Bacteriology 153: 163; and Hinnen et al., 1978, Proceedings of the National Academy of Sciences USA 75: 1920.

Materials and Methods
Strains and Plasmids
Strains

*E. coli* DH12S (available from Gibco BRL) is used for yeast plasmid rescue.

*Saccharomyces cerevisiae* YNG318: MATa Dpep4[cir+] ura3-52, leu2-D2, h is 4-539 is described in J. Biol. Chem. 272 (15): 9720-9727, 1997).

Plasmids

All yeast expression vectors are *S. cerevisiae* and *E. coli* shuttle vectors under the control of TPI promoter, constructed from pJCO$_{39}$ described in WO 00/10038.

Genes

Der p 1 from *Dermatophagoides pteronyssinus*: NCBI accession number: P08176, the amino acid sequence is shown in SEQ ID NO: 3.

The Cystein protease gene from *Trifolium repens* L (white clover) is the sequence which is deposited as EMBL: AY192363.

The alpha-factor (pheromone required for yeast mating) gene is the sequence in the commercial available pPICZα A vector from Invitrogen.

The trypsin gene from *Fusarium oxysporum* is the sequence which is deposited as EMBL: S63827 and for which the cDNA sequence is shown in SEQ ID NO: 6.

The phytase gene from *Peniophora lycii* strain CBS 686.96 is the sequence which is deposited as EMBL: PLY310696 and for which the cDNA sequence is shown in SEQ ID NO: 8.

Primers
For Expression of a Cellulase from *Mucor circinellides*

```
For cDNA cloning:
MCE-BC1 F (44mer):
                                        (SEQ ID NO: 10)
5'-CAACTGGTGATCACCACCATGAAGTTCACCGTTGCTATTACTTC-3'

MCE-Nru R (39mer):
                                        (SEQ ID NO: 11)
5'-TCTCGAGCTCGCGATTACTTTCTTTCGCAACCTGAGCGAG-3'

For yeast vector construction:
M61 F (50mer):
                                        (SEQ ID NO: 12)
5'-CCAGCTTCCGCAAACAAAGTCGCCAACATGAAGTTCACCGTTGCTA
TTAC-3'

M61Cutisig F (50mer):
                                        (SEQ ID NO: 13)
5'-CGCCAGCCTTGTTGCTGCTCTCCCCGCCGCTTCTTGCAGCTCTGTC
TATG-3'

C-term R61 R (49mer):
                                        (SEQ ID NO: 14)
5'-TAATTACATGATGCGGCCCTCTAGATTACTTTCTTTCGCAACCTGA
GCG-3'
```

For Expression of Cystein Protease from *Trifolium repens* L

```
alpha-signal-MunI (49mer):
                                        (SEQ ID NO: 15)
5'-ATAAACGACGGGACCCGGGGATCCAATTGATGAGATTCCCATCAAT
TTT-3' alpha-signal-CysPro R (42mer):
                                        (SEQ ID NO: 16)
5'-GCCCACGATGGAGAAATCGCGAGCTTCAGCTTCTCTTTTCTC-3' alpha-signal-CysPro F (42mer):
                                        (SEQ ID NO: 17)
5'-GAAAAAGAGAAGCTGAAGCTCGCGATTTCTCCATCGTGGGC-3'

Spe-CysPro R (50mer):
                                        (SEQ ID NO: 18)
5'-ACTAATTACATGATGCGGCCCACTAGTTCATTTCTTCTTAGTAGGA
TAAG-3'

Cuti-Sig-CysPro (50mer):
                                        (SEQ ID NO: 19)
5'-GCACCGCCAGCCTTGTTGCTGCTCTCCCCCGCGATTTCTCCATCGT
GGGC-3'

CysPro C-term (50mer):
                                        (SEQ ID NO: 20)
5'-TAATTACATGATGCGGCCCGCGGCCGCTCATTTCTTCTTAGTAGGA
TAAG-3'
```

For Expression of Trypsin from *Fusarium*

```
yeast-F (43mer):
                                        (SEQ ID NO: 21)
5'-ACGACGGTACCCGGGGATCAAGCTTATGGTCAAGTTCGCTTCC-3' yeast-R (43mer):
                                        (SEQ ID NO: 22)
5'-AACTAATTACATGATGCGGCCCTCTAGATTAAGCATAGGTGTC-3'
```

```
cuti-pre (45mer):
                                                  (SEQ ID NO: 23)
5'-CGTTCCTGAACTTGTTGCCCGGGTTGGTGGCACTTCTGCCAGCGC-3'

TP2-Kex F (32mer):
                                                  (SEQ ID NO: 24)
5'-GTTCCTGAACTTGTTCGGCGGGTTGGTGGCAC-3'

TP2-Kex R (32mer):
                                                  (SEQ ID NO: 25)
5'-GTGCCACCAACCCGCCGAACAAGTTCAGGAAC-3'

Cuti-pre F (29mer):
                                                  (SEQ ID NO: 26)
5'-GTTGCTGCTCTCCCCGTTGGTGGCACTTC-3'

Cuti-pre R (29mer):
                                                  (SEQ ID NO: 27)
5'-GAAGTGCCACCAACGGGGAGAGCAGCAAC-3'

CUTIpre-TPpro F (42mer):
                                                  (SEQ ID NO: 28)
5'-TCCTCAGGAGATCCCCAACATTGTTGGTGGCACTTCTGCCAG-3'

CUTIpre-TPpro R (40mer):
                                                  (SEQ ID NO: 29)
5'-GTTGGGGATCTCCTGAGGAGCGGGGAGAGCAGCAACAAGG-3'
```

For Expression of a Phytase from *Peniophora*

```
PP 1F (50mer):
                                                  (SEQ ID NO: 30)
5'-AAACGACGGTACCCGGGGATCAAGCTTATGGTTTCTTCGGCATTCG
CACC-3'

PP R (50mer):
                                                  (SEQ ID NO: 31)
5'-ACTAATTACATGATGCGGCCCTCTAGACTATTCCGACGGAACAAAG
CCGC-3'

PP 2F (50mer):
                                                  (SEQ ID NO: 32)
5'-CCGCCAGCCTTGTTGCTGCTCTCCCCCAGCTACCTATCCCCGCACA
AAAC-3'
```

Medium and Substrates

RS-25: 40 g/L soy bean powder, 40 g/L glucose, 10 g/L $KH_2PO_4$, 0.25 g/L $MgSO_4$, 0.01 g/L $FeSO_4$, 2.5 g/L $NH_4NO_3$; pH 6

YPD: 20 g/L Glucose, 20 g/L Pepton and 10 g/L Yeast extract

10× Basal solution: 66.8 g/l Yeast nitrogen base w/o amino acids (DIFCO), 100 g/l succinate and 60 g/l NaOH.

SC-glucose (or SC-medium): 100 ml/120% glucose (i.e., a final concentration of 2%=2 g/100 ml), 4 ml/15% threonine, 10 ml/11% tryptophan, 25 ml/120% casamino acids and 100 ml/l 10× basal solution. This solution was sterilized using a filter of a pore size of 0.20 micron. Agar and $H_2O$ (approx. 761 ml) is autoclaved together, and the separately sterilized SC-glucose solution is added to the agar solution.

PEG/LiAc solution: 50 ml 40% PEG4000 (sterilized by autoclaving) and 1 ml 5 M lithium acetate (sterilized by autoclaving).

Methods

Yeast Transformation

This method was used in examples 2-5.

To transform yeast the in vivo recombinant mechanism was utilized by which it is possible for yeast to recombine a vector sequence and PCR fragments in vivo to create an expression vector, if both the vector sequence and the PCR fragments have the same flanking regions.

A DNA mixture was prepared by mixing 0.5 Microl of vector (EcoRI-NotI digested) and 1 Microl of PCR fragments. *S. cerevisiae* YNG318 competent cells were thawed on ice. One hundred Microl of the cells were mixed with the DNA mixture and 10 Microl of carrier DNA (Clontech) in 12 ml polypropylene tubes (Falcon 2059). To this 0.6 ml PEG/LiAc solution was added and mixed gently and then incubated for 30 min at 30° C., and 200 rpm. Thereafter it was incubated for 30 min at 42° C. (heat shock) before transferring it to an eppendorf tube and centrifugation for 5 sec. The supernatant was removed and resolved in 3 ml of YPD. The cell suspension was then incubated for 45 min at 200 rpm at 30° C. before it was poured on to SC-glucose plates.

PCR Reaction

Unless otherwise indicated the PCR reactions were carried out under the following conditions:

The PCR reaction contained 38.9 MicroL H2O, 5 MicroL 10× reaction buffer, 1 MicroL Klen Taq LA (Clontech), 4 MicroL 10 mM dNTPs, 0.3 MicroL×2 100 µmol/MicroL primer and 0.5 MicroL template DNA and was carried out under the following conditions: 30 cycles of 10 sec at 98° C. and 90 sec at 68° C., and a final 10 min at 68° C.

Sandwich ELISA

Immunoplates (Nunc Maxisorb; Nunc-Nalgene) were coated overnight at 4° C. with at suitable dose of polyclonal rabbit anti Der p 1 antibody. The plates were then washed thoroughly with 0.15 M Phosphate Buffered Saline (PBS) containing 0.05% Tween 20 (PBST), and remaining binding sites are blocked with PBS with 2% skim milk powder, 1 h at room temperature. Samples, it can be purified, semi-purified recombinant group 1 mite polypeptide variant allergen or crude culture broth containing protein of interest, were added in a suitable dose or dose-range. The plates were then washed thoroughly with 0.15 M PBST before the allergens were detected by incubation with biotinylated monoclonal anti Der p 1 antibody (INDOOR) 1 h at room temperature. The plates were then washed again in 0.15 M PBST before conjugated with complexes of Streptavidin: Horse Radish Peroxidase (Kierkegaard & Perry) for 1 h at room temperature. The washing step was repeated and then the plates were developed by adding 3,3',5,5'-tetramethylbenzidine hydrogen peroxide (TMB Plus, Kem-En-Tec) before the reaction was stopped by addition of 0.2 M H2SO4. The optical density (OD) at 450 nm reflected allergen binding to the immunoglobin, and it was then possible to detect and also determine the amount of allergen bound by comparing with the data obtained for natural Der p 1 (available from Indoor biotechnologies, NA-DP1) which was included in the ELISA in a known concentration dose range.

Other Methods

*E. coli* transformation to rescue yeast plasmid was carried out by electroporation (B10-RAD Gene Pulser).

DNA Plasmids were prepared with the Qiagen® Plasmid Kit. DNA fragments and recovered from agarose gel by the Qiagen gel extraction Kit.

PCR was carried out by the PTC-200 DNA Engine.

The ABI PRISM™ 310 Genetic Analyzer was used for determination of all DNA sequences. Yeast total DNA was extracted by the Robzyk and Kassir's method described in Nucleic Acids Research 20(14): 3790 (1992).

Enzyme Assays

Cystein Protease Assay 96 well microtiter plate assay:

The following was added to each well: 10 MicroL 0.5 M Sodium acetate buffer (pH 5), 10 MicroL 2 M NaCl (comprising 700 MicroL mercaptethano/100 ml), 45 MicroL D.W. (distilled water) and 10 MicroL enzyme sample. The plate was then incubated at room temperature for 5-10 min (for maturation of the peptidase) before 25 MicroL 40 MicroM Z-Phe-Arg-MCA (0.1% DMSO) was added. Finally, the emission of MCA (4-methyl-coumaryl-7-amide) at 460 nm was measured in a fluorometer.

Trypsin Assay (PNA Assay for *Fusarium* Trypsin)
Substrate:

Fifty mg of N alpha-Benzoyl-DL-Arginine-p-Nitroanilide (BAPNA, Sigma B-4875) was dissolved in 1 ml DMSO and kept at −20° C. This solution was diluted 100× in the assay buffer just before use.

Assay Buffer:

50 mM Borate-NaOH (pH 10.5)+2 mM $CaCl_2$

Method:

20 Microl sample and 200 Microl assay buffer were mixed in a 96-well microtiter tray and Delta OD/min was measured at 405 nm for 5 min.

Phytase Assay

Ten MicroL diluted enzyme samples (diluted in 0.1 M sodium acetate, 0.01% Tween20, pH 5.5) were added into 250 MicroL of 5 mM sodium phytate (Sigma) in 0.1 M sodium acetate, 0.01% Tween20, pH 5.5 (pH adjusted after dissolving the sodium phytate; the substrate was preheated) and incubated for 30 minutes at 37° C. The reaction was stopped by adding 250 MicroL 10% TCA and free phosphate was measured by adding 500 MicroL 7.3 g $FeSO_4$ in 100 ml molybdate reagent (2.5 g $(NH_4)_6Mo7O_{24}.4H_2O$ in 8 ml $H_2SO_4$ diluted to 250 ml). The absorbance at 750 nm was measured on 200 MicroL samples in 96 well microtiter plates. Substrate and enzyme blanks were included. A phosphate standard curve was also included (0-2 mM phosphate). 1 U equals the amount of enzyme that releases 1 Micromol phosphate/min at the given conditions.

EXAMPLES

Example 1

Expression of Der p 1 in *S. cerevisiae*

The Der p 1 cystein protease from *Dermantophagoides pteronyssinus* (the amino acid sequence of which is depicted in SEQ ID NO: 3) encoding gene was located in vector pSteD212, which is derived from yeast expression vector pYES 2.0 (Invitrogen, Kofod et al., 1994, J. Biol. Chem. 269: 29182-29189 and Christgau et al., 1994, Biochem. Mol. Biol. Int. 33: 917-925).

This plasmid replicated both in *E. coli* and in *S. cerevisiae*. In *S. cerevisiae* Der p 1 was expressed from this plasmid.

Recombinant Der p 1 was expressed with the Der p 1 propeptide and had the mutation S54N or N52Q which disrupts the only N-glycosylation motif within the mature sequence.

For secretion in yeast two different signal peptides were tested for their expression efficiency by introducing them upstream of the encoding pro-Der p 1 gene. Expression constructs with signal peptides were made by cloning of DNA fragments (Sambrook et al., Molecular Cloning: A Laboratory Manual, 2nd Ed., Cold Spring Harbor, 1989). One signal peptide was the natural occurring *Dermantophagoides pteronyssinus* Der p 1 signal peptide with the amino acid sequence MKIVLAIASLLALSAVYA (SEQ ID NO: 3) and the other signal peptide was derived from a cutinase from *Humicula insolens* with the amino acid sequence MKFFTTIL-STASLVAALP (SEQ ID NO: 1). The yeast strain and the construct with the dust mite Der p 1 signal peptide was named pre-pro-Der p 1 and the yeast strain and construct with the cutinase signal peptide was named cuti-pro-Der p 1.

The constructs were transformed into *S. cerevisiae*. For screening of yeast transformants expressing Der p 1, the transformation solution was plated on SC-agar plates for colony formation at 30° C. for 3 days. Colonies were inoculated in 50 ml sterile plastic tubes, each tube containing 10 mL SC medium. The tubes were fermented in 500 ml baffled Erlenmeyer flasks containing 100 ml SC medium at 30° C., 250 rpm for 4 days. Culture broth from these fermentations were used for sandwich ELISA experiments to determine the concentration of expressed protein.

The expression level of Der p 1 by the pre-pro Der p1 S54N and the pre-pro Der p1 N52Q transformants were determined by sandwich ELISA as described above in the Method section to be at the same level plus/minus 8%. It was concluded that the expression level of the two strains with the pre-pro-Der p 1 was independent of which of the two mutations S54N and N52Q were used.

In another experiment, 4.5 L culture broth of pre-pro-Der p 1 (N52Q) and cuti-pro-Der p 1 (S54N) were fermented for 4 days and samples were taken each day during fermentation and the amount of Der p 1 was measured by the Sandwich ELISA as described above to follow the expression level. The ratio between expression yields of cuti-pro-Der p 1 and pre-pro-Der p 1 is shown below.

| Fermentation day | Expression yield (cuti-pro Der p 1/pre-pro-Der p 1) |
|---|---|
| Day 1 | 8 |
| Day 2 | 10 |
| Day 3 | 8 |
| Day 4 | 6 |

For each day of fermentation the cuti-pro-Der p 1 expressed between 6-10 times more Der p 1 than pre-pro-Der p 1 which showed that the cutinase signal peptide in front of pro-Der p 1 increased the expression level of pro-Der p 1 protein compared to the use of natural dust mite Der p 1 signal peptide.

Example 2

Expression of a Cellulase from *Mucor circinellides* in *S. cerevisiae*

*Mucor circinellides* IFO4554 was cultivated in shake flask containing RS-25+0.5% lactose medium for one day at 30° C. The mycelium was collected and used for mRNA preparation, which was subsequently reverse transcribed into cDNA. An approximately 1 kb fragment was amplified by PCR from the cDNA by using the MCE-BC1 F and MCE-Nru R primer pair and the following PCR conditions: 2 min at 94° C.; 35 cycles of 1 min at 94° C., 1 min at 45° C. and 2.5 min at 72° C.; and finally 8 min at 72° C. The amplified fragment was cloned into T-vector (Novagene).

The fragment (the *Mucor* cellulase gene) in T-vector was re-amplified with the primer pairs, M61 F and C-term R61 R, and M61 Cutisig F and C-term R61 R, where the former pair was used for the construct with the original signal sequence (the signal sequence of the *Mucor* cellulase gene) and the latter pair was used to construct a nucleic acid sequence comprising the signal sequence from the *H. insolens* cutinase (SEQ ID NO: 2) and the *Mucor* cellulase gene.

Yeast was transformed by introducing the resulting PCR fragments into *S. cerevisiae* YNG318 together with the pJC039 vector digested with HindIII and XbaI, and PvuII and XbaI, respectively.

The obtained transformants were cultivated in 24 well plates containing YPD medium at 30° C. and 180 rpm for 3 days. The culture supernatants were applied to holes in an agar plated containing 0.2% CMC (carboxy methyl cellulose), pH 8.5. In below table the size of the halos surrounding holes containing culture supernatant from yeast cells expressing the cellulase from *Mucor* with either the *H. insolens* cutinase signal peptide or with the signal peptide from the *Mucor* cellulase gene. As the cellulase is capable of degrading the CMC thereby creating the halo the size of the halo correlates to the amount of cellulase present in the culture supernatant which was placed in the particular hole. Thus a large halo indicates high amounts of cellulase while a small halo indicates a low amount of cellulase.

|  | Halo size in CMC plate |
|---|---|
| *Mucor* cellulase with *H. insolens* cutinase signal peptide | +++++ |
| *Mucor* cellulase with its own signal peptide | (+) |

The results indicate that the expression level in yeast of *Mucor* cellulase is much higher when it is expressed with the signal peptide sequence from the *H. insolens* cutinase gene than when expressed with its own signal peptide sequence (*Mucor* cellulase gene).

Example 3

Expression of Cystein Protease from *Trifolium repens* L in *S. Cerevisiae*

To construct an expression vector comprising the signal peptide from alpha-factor and the cystein protease from *Trifolium repens* L, the DNA fragment encoding the alpha-factor signal peptide was re-amplified with a primer pair, alpha-signal-MunI and alpha-signal-CysProR. The gene encoding pro-mature region of the cystein protease from *Trifolium repens* L was re-amplified with a primer pair, alpha-signal-CysPro F and Spe-Cys ProR using the EMBL:AY192363 sequence as template. Yeast was transformed by mixing these two PCR fragments together with pJC039 vector digested with Hind III and Xba I and introduced into *S. cerevisiae* YNG318.

To construct an expression vector comprising the signal peptide from the *H. insolens* cutinase and the cystein protease from *Trifolium repens* L, the gene encoding the pro-mature region of the cystein protease from *Trifolium repens* L was re-amplified with a primer pair, Cuti-Sig-CysPro and CysPro C-term. Yeast was transformed by mixing the obtained PCR fragment with pJC039 vector digested with Hind III and Xba I and introduced into *S. cerevisiae* YNG318.

The obtained transformants were cultivated in 24 well plate containing 1 ml of YPD at 27° C. for 3 days and then the supernatants were tested for cystein protease activity as described in the Methods section. The measurements of the cystein protease activity are shown in below table.

|  | Cystein protease activity (fluorescence emission/min) |
|---|---|
| Cystein protease with *H. insolens* cutinase signal peptide | $4.446 \times 10^6$ |
| Cystein protease with alpha-factor signal peptide | $4.073 \times 10^5$ |

The results indicate that the expression level in yeast of the cystein protease from white clover is 10 times higher when the protease is expressed with the *H. insolens* cutinase signal peptide than with the alpha-factor signal peptide.

Example 4

Expression of Trypsin from *Fusarium* in *S. Cerevisiae*

The trypsin gene from *Fusarium* was re-amplified with the primer pairs, yeast-F and yeast-R, and cuti-pre and yeast-R using the EMBL: S63827 sequence as template, i.e. the cDNA sequence shown in SEQ ID NO: 6. The yeast-F/yeast-R primer pair was used to construct a sequence comprising a nucleic acid sequence encoding the signal peptide, the pro-region and the mature part of the trypsin gene, while the cuti-pre/yeast-R primer pair was used to construct a nucleic acid sequence comprising the signal peptide and pro-region from the *H. insolens* cutinase and the mature trypsin gene from *Fusarium*. Yeast was transformed introducing the resulting PCR fragments into *S. cerevisiae* YNG318 together with the pJC039 vector digested with HindIII and XbaI, and PvuII and XbaI.

The obtained transformants (pTM-TP1 and pTM-TP2) were cultivated in 24 well plates containing YPD medium at 30° C., 180 rpm for 3 days.

pTM-TP1: *Fusarium* Trypsin signal+ *Fusarium* Trypsin Pro+ mature trypsin pTM-TP2: *H. insolens* cutinase signal+ *H. insolens* cutinase Pro+ mature trypsin The trypsin activity was measured as described above in the Method section. No activity was observed in both culture supernatant even with Neutrase™ (as a maturase) addition. However, the pro-form of trypsin (cutinase pro+mature trypsin) was detected by Western blotting with pTM-TP2.

Therefore, the following constructs were made:

pTM-TP2-Kex: *H. insolens* cutinase signal peptide+ *H. insolens* cutinase pro-region+KexII site+ mature *Fusarium* trypsin pTM-TP2w/o pro: *H. insolens* cutinase signal peptide+ mature *Fusarium* trypsin pTM-TP2 TPpro: *H. insolens* cutinase signal peptide+ *Fusarium* trypsin pro-region+ *Fusarium* mature trypsin Each of the primer pairs, TP2-Kex F and R, Cuti-pre F and R and CUTI-pre-TPpro F and R, were used to prepare pTM-TP2-Kex, pTM-TP2w/o pro and pTM-TP2 TPpro, respectively by mixing them with pTM-TP2 vector digested with EagI and introducing this mixture into *S. cerevisiae* YNG318.

The obtained transformants were cultivated in 24 well plates containing YPD medium at 30° C., 180 rpm for 3 days.

| Construct | Signal peptide | Pro-region | Activity w/o Neutrase (as a maturase) | Activity with Neutrase | Western blot of cell extract (intracellular) | Western blot of supernatant (extracellular) |
|---|---|---|---|---|---|---|
| pTM-TP1 | Trypsin | Trypsin | – | – | Pro-form | – |
| pTM-TP1Kex | Trypsin | Trypsin (+ kex site) | – | – | Pro-form | – |
| pTM-TP2 | Cutinase | Cutinase | – | – | – | Pro-form |
| pTM-TP2Kex | Cutinase | Cutinase (+ kex site) | – | – | N.T. | N.T. |
| pTM-TP2 w/o pro | Cutinase | None | – | – | – | Larger than mature |
| pTM-TP2TPpro | Cutinase | Trypsin | – | + | – | Pro-form | wherein "–" means that no activity or no band in the Western blot could be detected, "+" means that trypsin activity was detectable, "pro-form" means that it was the pro-form of the trypsin which was detectable, "N.T." means "not tested" and for the pTM-TP2 w/o pro means that a protein larger than the mature was detectable, however this construct was designed not to include a pro-region, thus it is not a pro-form.

Trypsin activity was detected with pTM-TP2TPpro vector when Neutrase™ was added to the supernatant (final conc. 0.5 AU/ml). The results indicate that the *Fusarium* trypsin's own signal peptide does not work efficiently in yeast for expression of trypsin, while the *H. insolens* cutinase signal peptide does. The pro-region (also called the pro-sequence) from the *Fusarium* trypsin (7 amino acids) seems to be necessary for proper folding and activation of the trypsin.

Example 5

Expression of a Phytase from *Peniophora* in *S. Cerevisiae*

The *Peniophora* phytase gene was amplified with the primer pairs (PP1 F and PP R, PP2 F and PPR using the EMBL: PLY310696 sequence as template, i.e. the cDNA sequence shown in SEQ ID NO: 8. The PP1 F/PP R primer pair was used to construct a nucleic acid sequence encoding the signal peptide from the *Peniophora* phytase gene and the mature protein of *Peniophora* phytase, while the PP2 F/PPR primer pan was used to construct a nucleic acid sequence encoding the signal peptide from the *H. insolens* cutinase gene and the mature *Peniophora* phytase protein. Yeast was transformed by introducing the resulting PCR fragments into *S. cerevisiae* YNG318 together with the pJC039 vector digested with HindIII and XbaI, and PvuII and XbaI.

The obtained transformants were cultivated in 24 well plates and 500 ml-shake flaks containing YPD medium at 30° C., 180 rpm for 3 days.

The pTMPP1 construct comprised the original signal peptide sequence from the *Peniophora* phytase, while the pTMPP2 construct comprised the *H. insolens* cutinase signal peptide sequence. The phytase activity was measured, as described in the Method section, in the culture supernatant of transformants comprising the pTMPP1 or the pTMPP2 construct which were culture either in 24-well plates or in a shake flask. The results are shown below.

|  | 24-well | Shake flask |
|---|---|---|
| pTMPP1 (phytase signal) | 1.8 U/ml | 1 U/ml |
| pTMPP2 (cutinase signal) | 6.9 U/ml | 13 U/ml |

The results show that the transformants comprising the pTMPP2 construct express more phytase activity than those comprising the pTMPP1 construct indicating that the *H. insolens* signal peptide increases expression of the phytase in yeast compared with the phytase's own signal peptide.

Example 6

Expression of Phytase from *Peniophora* in *Aspergillus oryzae*

The constructs comprising the phytase gene with its own signal peptide sequence and the phytase gene with the *H. insolens* cutinase signal peptide sequence described in example 5 were used to construct an expression vector for *Aspergillus* and transformed into *Aspergillus* as described in Lassen et al., 2001, Applied and Environmental Micorbiology, 67: 4701-4707. For each of the constructs 49 strains were isolated, purified and the production of phytase was measured as described in the Method section above by culturing said transformants in shake flasks. When comparing the strains from the two groups of construct which expressed the highest level of phytase, it was found that the strain comprising the construct with the cutinase signal peptide expressed approximately 1.4 times more phytase than the one comprising the phytase signal peptide. Similarly, when the average amount of expressed phytase in the 5 strains from each group which expressed the highest amount of phytase was compared the strains comprising the construct with the cutinase signal peptide expressed approximately 1.3 times more phytase than those comprising the construct with the phytase signal peptide.

The invention claimed is:

1. A method for producing an enzyme, comprising cultivating a fungal host cell in a medium conducive for the production of an enzyme, wherein the host cell comprises a nucleic acid construct comprising a first nucleotide sequence encoding a signal peptide operably linked to a second nucleotide sequence encoding the enzyme, wherein the first nucleotide sequence is foreign to the second nucleotide sequence, the 3' end of the first nucleotide sequence is immediately upstream of the second nucleotide sequence, and the first nucleotide sequence is selected from the group consisting of:

(i) a nucleotide sequence encoding a signal peptide amino acid sequence having at least 90% sequence identity with SEQ ID NO:1 wherein the signal peptide retains the ability to direct the enzyme out of the fungal host cell, and (ii) a nucleotide sequence having at least 90% sequence identity with SEQ ID NO:2 and that encodes a signal peptide wherein the signal peptide retains the ability to direct the enzyme out of the fungal host cell.

2. The method of claim 1, wherein the first nucleotide sequence encodes a signal peptide amino acid sequence that has at least 95% sequence identity with SEQ ID NO:1.

3. The method of claim 1, wherein the first nucleotide sequence consists of SEQ ID NO:2.

4. The method of claim 1, wherein the first nucleotide sequence has at least 97% sequence identity with SEQ ID NO:2.

5. The method of claim 1, wherein the second nucleotide sequence encodes a heterologous enzyme.

6. The method of claim 1, wherein the fungal host cell contains one or more copies of the second nucleotide sequence.

7. The method of claim 1, wherein the second nucleotide sequence encodes an enzyme selected from the group consisting of oxidoreductase, transferase, hydrolase, lyase, isomerase, and ligase.

8. The method of claim 1, wherein the enzyme is selected from the group consisting of aminopeptidase, amylase, carbohydrase, carboxypeptidase, catalase, cellulase, cellobiohydrolase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, and beta-xylosidase.

9. The method of claim 1, wherein the enzyme is amylase.

10. The method of claim 1, wherein the enzyme is phytase.

11. The method of claim 1, wherein the fungal host cell is selected from the group consisting of *Acremonium, Aspergillus, Fusarium, Humicola, Mucor, Myceliophthora, Neurospora, Penicillium, Thielavia, Tolypocladium*, and *Trichoderma*.

12. The method of claim 1, wherein the fungal host cell is selected from the group consisting of *Aspergillus awamori, Aspergillus foetidus, Aspergillus japonicus, Aspergillus nidulans, Aspergillus niger* and *Aspergillus oryzae*.

13. The method of claim 1, wherein the fungal host cell is selected from the group consisting of *Trichoderma reesei, Trichoderma longibrachiatum, Trichoderma viride*.

14. The method of claim 1, wherein the fungal host cell is *Aspergillus* and the enzyme is phytase.

15. The method of claim 1 comprising the step of isolating the enzyme from the cultivation medium; wherein the enzyme was secreted from the host cell.

* * * * *

SEQUENCE LISTING

<160> NUMBER OF SEQ ID NOS: 32

<210> SEQ ID NO 1
<211> LENGTH: 18
<212> TYPE: PRT
<213> ORGANISM: Humicola insolens

<400> SEQUENCE: 1

Met Lys Phe Phe Thr Thr Ile Leu Ser Thr Ala Ser Leu Val Ala Ala
1               5                   10                  15

Leu Pro

<210> SEQ ID NO 2
<211> LENGTH: 54
<212> TYPE: DNA
<213> ORGANISM: Humicola insolens

<400> SEQUENCE: 2
atgaagttct tcaccaccat cctcagcacc gccagccttg ttgctgctct cccc          54

<210> SEQ ID NO 3
<211> LENGTH: 320
<212> TYPE: PRT
<213> ORGANISM: Dermatophagoides pteronyssinus
<220> FEATURE:
<221> NAME/KEY: SIGNAL
<222> LOCATION: (1)..(18)
<220> FEATURE:
<221> NAME/KEY: PROPEP
<222> LOCATION: (19)..(98)
<220> FEATURE:
<221> NAME/KEY: mat_peptide
<222> LOCATION: (99)..(320)

<400> SEQUENCE: 3

Met Lys Ile Val Leu Ala Ile Ala Ser Leu Leu Ala Leu Ser Ala Val
            -95                 -90                 -85

Tyr Ala Arg Pro Ser Ser Ile Lys Thr Phe Glu Glu Tyr Lys Lys Ala
        -80                 -75                 -70

Phe Asn Lys Ser Tyr Ala Thr Phe Glu Asp Glu Glu Ala Ala Arg Lys
        -65                 -60                 -55

Asn Phe Leu Glu Ser Val Lys Tyr Val Gln Ser Asn Gly Gly Ala Ile
-50                 -45                 -40                 -35

Asn His Leu Ser Asp Leu Ser Leu Asp Glu Phe Lys Asn Arg Phe Leu
            -30                 -25                 -20

Met Ser Ala Glu Ala Phe Glu His Leu Lys Thr Gln Phe Asp Leu Asn
            -15                 -10                 -5

Ala Glu Thr Asn Ala Cys Ser Ile Asn Gly Asn Ala Pro Ala Glu Ile
-1  1                   5                   10

Asp Leu Arg Gln Met Arg Thr Val Thr Pro Ile Arg Met Gln Gly Gly
15                  20                  25                  30

Cys Gly Ser Cys Trp Ala Phe Ser Gly Val Ala Ala Thr Glu Ser Ala
                35                  40                  45

Tyr Leu Ala Tyr Arg Asn Gln Ser Leu Asp Leu Ala Glu Gln Glu Leu
                50                  55                  60

Val Asp Cys Ala Ser Gln His Gly Cys His Gly Asp Thr Ile Pro Arg
            65                  70                  75

Gly Ile Glu Tyr Ile Gln His Asn Gly Val Val Gln Glu Ser Tyr Tyr
            80                  85                  90

Arg Tyr Val Ala Arg Glu Gln Ser Cys Arg Arg Pro Asn Ala Gln Arg
95                  100                 105                 110

Phe Gly Ile Ser Asn Tyr Cys Gln Ile Tyr Pro Pro Asn Val Asn Lys
                115                 120                 125

Ile Arg Glu Ala Leu Ala Gln Thr His Ser Ala Ile Ala Val Ile Ile
            130                 135                 140

```
Gly Ile Lys Asp Leu Asp Ala Phe Arg His Tyr Asp Gly Arg Thr Ile
            145                 150                 155
Ile Gln Arg Asp Asn Gly Tyr Gln Pro Asn Tyr His Ala Val Asn Ile
160                 165                 170
Val Gly Tyr Ser Asn Ala Gln Gly Val Asp Tyr Trp Ile Val Arg Asn
175                 180                 185                 190
Ser Trp Asp Thr Asn Trp Gly Asp Asn Gly Tyr Gly Tyr Phe Ala Ala
                195                 200                 205
Asn Ile Asp Leu Met Met Ile Glu Glu Tyr Pro Tyr Val Val Ile Leu
                210                 215                 220

<210> SEQ ID NO 4
<211> LENGTH: 316
<212> TYPE: PRT
<213> ORGANISM: Mucor circinellides
<220> FEATURE:
<221> NAME/KEY: mat_peptide
<222> LOCATION: (1)..(316)

<400> SEQUENCE: 4

Ala Ser Cys Ser Ser Val Tyr Gly Gln Cys Gly Gly Ile Gly Trp Ser
1               5                   10                  15
Gly Pro Thr Cys Cys Gln Ser Gly Ser Thr Cys Val Ala Gln Glu Gly
            20                  25                  30
Asn Lys Tyr Tyr Ser Gln Cys Leu Pro Gly Ser His Ser Asn Asn Ala
        35                  40                  45
Gly Asn Ala Ser Ser Thr Lys Lys Thr Ser Thr Lys Ser Ser Thr Thr
    50                  55                  60
Thr Ala Lys Ala Thr Ala Thr Val Thr Thr Lys Thr Val Thr Lys Thr
65                  70                  75                  80
Thr Thr Lys Thr Thr Thr Lys Thr Ser Thr Ala Ala Ala Ser Thr
                85                  90                  95
Ser Thr Ser Ser Ser Ala Gly Tyr Lys Val Ile Ser Gly Gly Lys Ser
                100                 105                 110
Gly Ser Gly Ser Thr Thr Arg Tyr Trp Asp Cys Cys Lys Ala Ser Cys
            115                 120                 125
Ser Trp Pro Gly Lys Ala Ser Val Thr Gly Pro Val Asp Thr Cys Ala
        130                 135                 140
Ser Asn Gly Ile Ser Leu Leu Asp Ala Asn Ala Gln Ser Gly Cys Asn
145                 150                 155                 160
Gly Gly Asn Gly Phe Met Cys Asn Asn Asn Gln Pro Trp Ala Val Asn
                165                 170                 175
Asp Glu Leu Ala Tyr Gly Phe Ala Ala Ala Ser Ile Ala Gly Ser Asn
                180                 185                 190
Glu Ala Gly Trp Cys Cys Gly Cys Tyr Glu Leu Thr Phe Thr Ser Gly
            195                 200                 205
Ala Ala Ser Gly Lys Lys Met Val Val Gln Val Thr Asn Thr Gly Gly
        210                 215                 220
Asp Leu Gly Ser Asn His Phe Asp Leu Gln Met Pro Gly Gly Gly Val
225                 230                 235                 240
Gly Ile Phe Asn Gly Cys Ala Ala Gln Trp Gly Ala Pro Asn Asp Gly
                245                 250                 255
Trp Gly Ala Arg Tyr Gly Gly Val Ser Ser Val Ser Asp Cys Ala Ser
                260                 265                 270
Leu Pro Ser Ala Leu Gln Ala Gly Cys Lys Trp Arg Phe Asn Trp Phe
            275                 280                 285
```

```
Lys Asn Ser Asp Asn Pro Thr Met Thr Phe Lys Glu Val Thr Cys Pro
        290                 295                 300

Ala Glu Leu Thr Thr Arg Ser Gly Cys Glu Arg Lys
305                 310                 315

<210> SEQ ID NO 5
<211> LENGTH: 327
<212> TYPE: PRT
<213> ORGANISM: Trifolium repens L
<220> FEATURE:
<221> NAME/KEY: mat_peptide
<222> LOCATION: (109)..(327)

<400> SEQUENCE: 5

Arg Asp Phe Ser  Ile Val Gly Tyr  Ser Glu Asp Leu Lys Ser Met
            -105             -100             -95

Asp Lys Leu Ile Glu Leu Phe Glu Ser Trp Met Ser Arg His Gly Lys
        -90             -85             -80

Ile Tyr Glu Thr Ile Glu Lys Leu Leu Arg Phe Glu Val Phe Lys
    -75             -70             -65

Asp Asn Leu Lys His Ile Asp Asp Arg Asn Lys Val Val Ser Asn Tyr
-60             -55             -50                         -45

Trp Leu Gly Leu Asn Glu Phe Ala Asp Leu Ser His Gln Glu Phe Lys
            -40             -35             -30

Asn Lys Tyr Leu Gly Leu Lys Val Asp Leu Ser Gln Arg Glu Ser
        -25             -20             -15

Ser Asn Glu Glu Glu Phe Thr Tyr Arg Asp Val Asp Leu Pro Lys Ser
        -10             -5              -1  1

Val Asp Trp Arg Lys Lys Gly Ala Val Thr Pro Val Lys Asn Gln Gly
5               10              15                          20

Gln Cys Gly Ser Cys Trp Ala Phe Ser Thr Val Ala Ala Val Glu Gly
            25              30              35

Ile Asn Gln Ile Val Thr Gly Asn Leu Thr Ser Leu Ser Glu Gln Glu
        40              45              50

Leu Ile Asp Cys Asp Thr Thr Tyr Asn Asn Gly Cys Asn Gly Gly Leu
55              60              65

Met Asp Tyr Ala Phe Ser Phe Ile Val Gln Asn Gly Gly Leu His Lys
70              75              80

Glu Asp Asp Tyr Pro Tyr Ile Met Glu Glu Ser Thr Cys Glu Met Lys
85              90              95                          100

Lys Glu Glu Thr Gln Val Val Thr Ile Asn Gly Tyr His Asp Val Pro
            105             110             115

Gln Asn Asn Glu Gln Ser Leu Leu Lys Ala Leu Ala Asn Gln Pro Leu
            120             125             130

Ser Val Ala Ile Glu Ala Ser Ser Arg Asp Phe Gln Phe Tyr Ser Gly
        135             140             145

Gly Val Phe Asp Gly His Cys Gly Ser Asp Leu Asp His Gly Val Ser
        150             155             160

Ala Val Gly Tyr Gly Thr Ser Lys Asn Leu Asp Tyr Ile Ile Val Lys
165             170             175                         180

Asn Ser Trp Gly Ala Lys Trp Gly Glu Lys Gly Phe Ile Arg Met Lys
            185             190             195

Arg Asn Ile Gly Lys Pro Glu Gly Ile Cys Gly Leu Tyr Lys Met Ala
            200             205             210

Ser Tyr Pro Thr Lys Lys Lys
        215
```

<210> SEQ ID NO 6
<211> LENGTH: 998
<212> TYPE: DNA
<213> ORGANISM: fusarium oxysporum
<220> FEATURE:
<221> NAME/KEY: CDS
<222> LOCATION: (58)..(804)

<400> SEQUENCE: 6

| | | |
|---|---|---|
| atcatcaacc actcttcact cttcaactct cctctcttgg atatctatct cttcacc | | 57 |
| atg gtc aag ttc gct tcc gtc gtt gca ctt gtt gct ccc ctg gct gct<br>Met Val Lys Phe Ala Ser Val Val Ala Leu Val Ala Pro Leu Ala Ala<br>1              5                  10             15 | | 105 |
| gcc gct cct cag gag atc ccc aac att gtt ggt ggc act tct gcc agc<br>Ala Ala Pro Gln Glu Ile Pro Asn Ile Val Gly Gly Thr Ser Ala Ser<br>              20                 25               30 | | 153 |
| gct ggc gac ttt ccc ttc atc gtg agc att agc cgc aac ggt ggc ccc<br>Ala Gly Asp Phe Pro Phe Ile Val Ser Ile Ser Arg Asn Gly Gly Pro<br>        35                  40               45 | | 201 |
| tgg tgt gga ggt tct ctc ctc aac gcc aac acc gtc ttg act gct gcc<br>Trp Cys Gly Gly Ser Leu Leu Asn Ala Asn Thr Val Leu Thr Ala Ala<br>50                 55                  60 | | 249 |
| cac tgc gtt tcc gga tac gct cag agc ggt ttc cag att cgt gct ggc<br>His Cys Val Ser Gly Tyr Ala Gln Ser Gly Phe Gln Ile Arg Ala Gly<br>65                 70                  75               80 | | 297 |
| agt ctg tct cgc act tct ggt ggt att acc tcc tcg ctt tcc tcc gtc<br>Ser Leu Ser Arg Thr Ser Gly Gly Ile Thr Ser Ser Leu Ser Ser Val<br>                  85                 90               95 | | 345 |
| aga gtt cac cct agc tac agc gga aac aac aac gat ctt gct att ctg<br>Arg Val His Pro Ser Tyr Ser Gly Asn Asn Asn Asp Leu Ala Ile Leu<br>                        100               105            110 | | 393 |
| aag ctc tct act tcc atc ccc tcc ggc gga aac atc ggc tat gct cgc<br>Lys Leu Ser Thr Ser Ile Pro Ser Gly Gly Asn Ile Gly Tyr Ala Arg<br>115                       120               125 | | 441 |
| ctg gct gct tcc ggc tct gac cct gtc gct gga tct tct gcc act gtt<br>Leu Ala Ala Ser Gly Ser Asp Pro Val Ala Gly Ser Ser Ala Thr Val<br>              130               135               140 | | 489 |
| gct ggc tgg ggc gct acc tct gag ggc ggc agc tct act ccc gtc aac<br>Ala Gly Trp Gly Ala Thr Ser Glu Gly Gly Ser Ser Thr Pro Val Asn<br>145                      150               155            160 | | 537 |
| ctt ctg aag gtt act gtc cct atc gtc tct cgt gct acc tgc cga gct<br>Leu Leu Lys Val Thr Val Pro Ile Val Ser Arg Ala Thr Cys Arg Ala<br>                       165               170            175 | | 585 |
| cag tac ggc acc tcc gcc atc acc aac cag atg ttc tgt gct ggt gtt<br>Gln Tyr Gly Thr Ser Ala Ile Thr Asn Gln Met Phe Cys Ala Gly Val<br>              180               185               190 | | 633 |
| tct tcc ggt ggc aag gac tct tgc cag ggt gac agc ggc ggc ccc atc<br>Ser Ser Gly Gly Lys Asp Ser Cys Gln Gly Asp Ser Gly Gly Pro Ile<br>195                      200               205 | | 681 |
| gtc gac agc tcc aac act ctt atc ggt gct gtc tct tgg ggt aac gga<br>Val Asp Ser Ser Asn Thr Leu Ile Gly Ala Val Ser Trp Gly Asn Gly<br>              210               215               220 | | 729 |
| tgt gcc cga ccc aac tac tct ggt gtc tat gcc agc gtt ggt gct ctc<br>Cys Ala Arg Pro Asn Tyr Ser Gly Val Tyr Ala Ser Val Gly Ala Leu<br>225                      230               235            240 | | 777 |
| cgc tct ttc att gac acc tat gct taa ataccttgtt ggaagcgtcg<br>Arg Ser Phe Ile Asp Thr Tyr Ala<br>                        245 | | 824 |
| agatgttcct tgaatattct ctagcttgag tcttggatac gaaacctgtt tgagaaatag | | 884 |
| gtttcaacga gttaagaaga tatgagttga ttcagttgg atcttagtcc tggttgctcg | | 944 |

```
taatagagca atctagatag cccaaattga atatgaaatt tgatgaaaat attc         998

<210> SEQ ID NO 7
<211> LENGTH: 248
<212> TYPE: PRT
<213> ORGANISM: fusarium oxysporum

<400> SEQUENCE: 7

Met Val Lys Phe Ala Ser Val Val Ala Leu Val Ala Pro Leu Ala Ala
1               5                   10                  15

Ala Ala Pro Gln Glu Ile Pro Asn Ile Val Gly Gly Thr Ser Ala Ser
            20                  25                  30

Ala Gly Asp Phe Pro Phe Ile Val Ser Ile Ser Arg Asn Gly Gly Pro
        35                  40                  45

Trp Cys Gly Gly Ser Leu Leu Asn Ala Asn Thr Val Leu Thr Ala Ala
    50                  55                  60

His Cys Val Ser Gly Tyr Ala Gln Ser Gly Phe Gln Ile Arg Ala Gly
65                  70                  75                  80

Ser Leu Ser Arg Thr Ser Gly Gly Ile Thr Ser Ser Leu Ser Ser Val
                85                  90                  95

Arg Val His Pro Ser Tyr Ser Gly Asn Asn Asn Asp Leu Ala Ile Leu
            100                 105                 110

Lys Leu Ser Thr Ser Ile Pro Ser Gly Gly Asn Ile Gly Tyr Ala Arg
        115                 120                 125

Leu Ala Ala Ser Gly Ser Asp Pro Val Ala Gly Ser Ser Ala Thr Val
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175

Gln Tyr Gly Thr Ser Ala Ile Thr Asn Gln Met Phe Cys Ala Gly Val
            180                 185                 190

Ser Ser Gly Gly Lys Asp Ser Cys Gln Gly Asp Ser Gly Gly Pro Ile
        195                 200                 205

Val Asp Ser Ser Asn Thr Leu Ile Gly Ala Val Ser Trp Gly Asn Gly
    210                 215                 220

Cys Ala Arg Pro Asn Tyr Ser Gly Val Tyr Ala Ser Val Gly Ala Leu
225                 230                 235                 240

Arg Ser Phe Ile Asp Thr Tyr Ala
                245

<210> SEQ ID NO 8
<211> LENGTH: 1568
<212> TYPE: DNA
<213> ORGANISM: peniophora lycii
<220> FEATURE:
<221> NAME/KEY: CDS
<222> LOCATION: (111)..(1427)
<220> FEATURE:
<221> NAME/KEY: sig_peptide
<222> LOCATION: (111)..(197)
<220> FEATURE:
<221> NAME/KEY: mat_peptide
<222> LOCATION: (198)..(1427)

<400> SEQUENCE: 8
catcttctgc tctgacctcc atctcgctga gcggccgacg agaacctagg ggctctaagt    60
ccacgtacta tcgccgcgcc tgtgaaggcc ccataccagc ccttatcgat atg gtt     116
                                                      Met Val
```

```
tct tcg gca ttc gca cct tcc atc cta ctt agc ttg atg tcg agt ctt      164
Ser Ser Ala Phe Ala Pro Ser Ile Leu Leu Ser Leu Met Ser Ser Leu
        -25             -20                 -15 gct ttg agc acg cag ttc agc ttt gtt gcg gcg cag cta cct atc ccc      212
Ala Leu Ser Thr Gln Phe Ser Phe Val Ala Ala Gln Leu Pro Ile Pro
        -10              -5              -1   1               5 gca caa aac aca agt aat tgg ggg cct tac gat ccc ttc ttt ccc gtc      260
Ala Gln Asn Thr Ser Asn Trp Gly Pro Tyr Asp Pro Phe Phe Pro Val
                 10                  15                  20 gaa ccg tat gca gct ccg ccg gaa ggg tgc aca gtg aca cag gtc aac      308
Glu Pro Tyr Ala Ala Pro Pro Glu Gly Cys Thr Val Thr Gln Val Asn
             25                  30                  35 ctg att cag agg cac ggc gcg cgt tgg ccc aca tcc ggc gcg cgg tcg      356
Leu Ile Gln Arg His Gly Ala Arg Trp Pro Thr Ser Gly Ala Arg Ser
         40                  45                  50 cgg cag gtc gcc gcc gta gcg aag ata caa atg gcg cga cca ttc acg      404
Arg Gln Val Ala Ala Val Ala Lys Ile Gln Met Ala Arg Pro Phe Thr
         55                  60                  65 gat ccc aag tat gag ttc ctc aac gac ttc gtg tac aag ttc ggc gtc      452
Asp Pro Lys Tyr Glu Phe Leu Asn Asp Phe Val Tyr Lys Phe Gly Val
70                   75                  80                  85 gcc gat ctg cta ccg ttc ggg gct aac caa tcg cac caa acc ggc acc      500
Ala Asp Leu Leu Pro Phe Gly Ala Asn Gln Ser His Gln Thr Gly Thr
             90                  95                 100 gat atg tat acg cgc tac agt aca cta ttt gag ggc ggg gat gta ccc      548
Asp Met Tyr Thr Arg Tyr Ser Thr Leu Phe Glu Gly Gly Asp Val Pro
                105                 110                 115 ttt gtg cgc gcg gct ggt gac caa cgc gtc gtt gac tcg tcg acg aac      596
Phe Val Arg Ala Ala Gly Asp Gln Arg Val Val Asp Ser Ser Thr Asn
            120                 125                 130 tgg acg gca ggc ttt ggc gat gct tct ggc gag act gtt ctc ccg acg      644
Trp Thr Ala Gly Phe Gly Asp Ala Ser Gly Glu Thr Val Leu Pro Thr
        135                 140                 145 ctc cag gtt gtg ctt caa gaa gag ggg aac tgc acg ctc tgc aat aat      692
Leu Gln Val Val Leu Gln Glu Glu Gly Asn Cys Thr Leu Cys Asn Asn
150                 155                 160                 165 atg tgc ccg aat gaa gtg gat ggt gac gaa tcc aca acg tgg ctg ggg      740
Met Cys Pro Asn Glu Val Asp Gly Asp Glu Ser Thr Thr Trp Leu Gly
                170                 175                 180 gtc ttt gcg ccg aac atc acc gcg cga ttg aac gct gct gcg ccg agt      788
Val Phe Ala Pro Asn Ile Thr Ala Arg Leu Asn Ala Ala Ala Pro Ser
            185                 190                 195 gcc aac ctc tca gac agc gac gcg ctc act ctc atg gat atg tgc ccg      836
Ala Asn Leu Ser Asp Ser Asp Ala Leu Thr Leu Met Asp Met Cys Pro
        200                 205                 210 ttc gac act ctc agc tcc ggg aac gcc agc ccc ttc tgt gac cta ttt      884
Phe Asp Thr Leu Ser Ser Gly Asn Ala Ser Pro Phe Cys Asp Leu Phe
    215                 220                 225 acc gcg gag gag tat gtg tcg tac gag tac tac tat gac ctc gac aag      932
Thr Ala Glu Glu Tyr Val Ser Tyr Glu Tyr Tyr Tyr Asp Leu Asp Lys
230                 235                 240                 245 tac tat ggc acg ggc ccc ggg aac gct ctc ggt cct gtc cag ggc gtc      980
Tyr Tyr Gly Thr Gly Pro Gly Asn Ala Leu Gly Pro Val Gln Gly Val
                250                 255                 260 gga tac gtc aat gag ctg ctt gca cgc ttg acc ggc caa gcc gtt cga     1028
Gly Tyr Val Asn Glu Leu Leu Ala Arg Leu Thr Gly Gln Ala Val Arg
            265                 270                 275 gac gag acg cag acg aac cgc acg ctc gac agc gac cct gca aca ttc     1076
Asp Glu Thr Gln Thr Asn Arg Thr Leu Asp Ser Asp Pro Ala Thr Phe
        280                 285                 290
```

-continued

```
ccg ctg aac cgt acg ttc tac gcc gac ttc tcg cat gat aac acc atg      1124
Pro Leu Asn Arg Thr Phe Tyr Ala Asp Phe Ser His Asp Asn Thr Met
295                 300                 305 gtg ccc atc ttt gcg gcg ctc ggg ctc ttc aac gcc acc gcc ctc gac      1172
Val Pro Ile Phe Ala Ala Leu Gly Leu Phe Asn Ala Thr Ala Leu Asp
310                 315                 320                 325 ccg ctg aag ccc gac gag aac agg ttg tgg gtg gac tct aag ctg gta      1220
Pro Leu Lys Pro Asp Glu Asn Arg Leu Trp Val Asp Ser Lys Leu Val
            330                 335                 340 ccg ttc tct gga cat atg acg gtc gag aag ctg gca tgt tct ggg aag      1268
Pro Phe Ser Gly His Met Thr Val Glu Lys Leu Ala Cys Ser Gly Lys
345                 350                 355 gag gcg gtc agg gtg ctc gtg aac gac gcg gtg cag ccg ctg gag ttc      1316
Glu Ala Val Arg Val Leu Val Asn Asp Ala Val Gln Pro Leu Glu Phe
360                 365                 370 tgc gga ggt gtt gat ggg gtg tgc gag ctt tcg gct ttc gta gag agc      1364
Cys Gly Gly Val Asp Gly Val Cys Glu Leu Ser Ala Phe Val Glu Ser
375                 380                 385 cag acg tat gcg cgg gag aat ggg caa ggc gac ttc gcc aag tgc ggc      1412
Gln Thr Tyr Ala Arg Glu Asn Gly Gln Gly Asp Phe Ala Lys Cys Gly
390                 395                 400                 405 ttt gtt ccg tcg gaa tagcgggaga ccgtctatgc tacacagtaa ttgtgtactc    1467
Phe Val Pro Ser Glu
            410 tatagcactg tagctgtact tacaagtcgt agggtacgat cgtacttacg ctcgtttatt   1527 gatccttcct ttaaaaaaaa aaaaaaaaaa aaaaaaaaa a                         1568

<210> SEQ ID NO 9
<211> LENGTH: 439
<212> TYPE: PRT
<213> ORGANISM: peniophora lycii

<400> SEQUENCE: 9

Met Val Ser Ser Ala Phe Ala Pro Ser Ile Leu Leu Ser Leu Met Ser
                -25                 -20                 -15

Ser Leu Ala Leu Ser Thr Gln Phe Ser Phe Val Ala Ala Gln Leu Pro
        -10                 -5                  -1   1

Ile Pro Ala Gln Asn Thr Ser Asn Trp Gly Pro Tyr Asp Pro Phe Phe
 5                  10                  15

Pro Val Glu Pro Tyr Ala Ala Pro Pro Glu Gly Cys Thr Val Thr Gln
20                  25                  30                  35

Val Asn Leu Ile Gln Arg His Gly Ala Arg Trp Pro Thr Ser Gly Ala
                40                  45                  50

Arg Ser Arg Gln Val Ala Ala Val Ala Lys Ile Gln Met Ala Arg Pro
            55                  60                  65

Phe Thr Asp Pro Lys Tyr Glu Phe Leu Asn Asp Phe Val Tyr Lys Phe
        70                  75                  80

Gly Val Ala Asp Leu Leu Pro Phe Gly Ala Asn Gln Ser His Gln Thr
    85                  90                  95

Gly Thr Asp Met Tyr Thr Arg Tyr Ser Thr Leu Phe Glu Gly Gly Asp
100                 105                 110                 115

Val Pro Phe Val Arg Ala Ala Gly Asp Gln Arg Val Val Asp Ser Ser
                120                 125                 130

Thr Asn Trp Thr Ala Gly Phe Gly Asp Ala Ser Gly Glu Thr Val Leu
            135                 140                 145

Pro Thr Leu Gln Val Val Leu Gln Glu Glu Gly Asn Cys Thr Leu Cys
        150                 155                 160
```

```
Asn Asn Met Cys Pro Asn Glu Val Asp Gly Asp Glu Ser Thr Thr Trp
    165                 170                 175

Leu Gly Val Phe Ala Pro Asn Ile Thr Ala Arg Leu Asn Ala Ala Ala
180                 185                 190                 195

Pro Ser Ala Asn Leu Ser Asp Ser Asp Ala Leu Thr Leu Met Asp Met
                200                 205                 210

Cys Pro Phe Asp Thr Leu Ser Ser Gly Asn Ala Ser Pro Phe Cys Asp
            215                 220                 225

Leu Phe Thr Ala Glu Glu Tyr Val Ser Tyr Glu Tyr Tyr Tyr Asp Leu
        230                 235                 240

Asp Lys Tyr Tyr Gly Thr Gly Pro Gly Asn Ala Leu Gly Pro Val Gln
    245                 250                 255

Gly Val Gly Tyr Val Asn Glu Leu Leu Ala Arg Leu Thr Gly Gln Ala
260                 265                 270                 275

Val Arg Asp Glu Thr Gln Thr Asn Arg Thr Leu Asp Ser Asp Pro Ala
                280                 285                 290

Thr Phe Pro Leu Asn Arg Thr Phe Tyr Ala Asp Phe Ser His Asp Asn
            295                 300                 305

Thr Met Val Pro Ile Phe Ala Ala Leu Gly Leu Phe Asn Ala Thr Ala
        310                 315                 320

Leu Asp Pro Leu Lys Pro Asp Glu Asn Arg Leu Trp Val Asp Ser Lys
    325                 330                 335

Leu Val Pro Phe Ser Gly His Met Thr Val Glu Lys Leu Ala Cys Ser
340                 345                 350                 355

Gly Lys Glu Ala Val Arg Val Leu Val Asn Asp Ala Val Gln Pro Leu
                360                 365                 370

Glu Phe Cys Gly Gly Val Asp Gly Val Cys Gly Leu Ser Ala Phe Val
            375                 380                 385

Glu Ser Gln Thr Tyr Ala Arg Glu Asn Gly Gln Gly Asp Phe Ala Lys
        390                 395                 400

Cys Gly Phe Val Pro Ser Glu
    405                 410

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
caactggtga tcaccaccat gaagttcacc gttgctatta cttc          44

<210> SEQ ID NO 11
<211> LENGTH: 40
<212> TYPE: DNA
<213> ORGANISM: Artificial Sequence
<220> FEATURE:
<223> OTHER INFORMATION: Primer

<400> SEQUENCE: 11
tctcgagctc gcgattactt tctttcgcaa cctgagcgag              40

<210> SEQ ID NO 12
<211> LENGTH: 50
<212> TYPE: DNA
<213> ORGANISM: Artificial Sequence
<220> FEATURE:
<223> OTHER INFORMATION: Primer
```

<400> SEQUENCE: 12
ccagcttccg caaacaaagt cgccaacatg aagttcaccg ttgctattac        50

<210> SEQ ID NO 13
<211> LENGTH: 50
<212> TYPE: DNA
<213> ORGANISM: Artificial Sequene
<220> FEATURE:
<223> OTHER INFORMATION: Primer

<400> SEQUENCE: 13
cgccagcctt gttgctgctc tccccgccgc ttcttgcagc tctgtctatg        50

<210> SEQ ID NO 14
<211> LENGTH: 49
<212> TYPE: DNA
<213> ORGANISM: Artificial Sequence
<220> FEATURE:
<223> OTHER INFORMATION: Primer

<400> SEQUENCE: 14
taattacatg atgcggccct ctagattact ttctttcgca acctgagcg         49

<210> SEQ ID NO 15
<211> LENGTH: 49
<212> TYPE: DNA
<213> ORGANISM: Artificial Sequence
<220> FEATURE:
<223> OTHER INFORMATION: Primer

<400> SEQUENCE: 15
ataaacgacg ggacccgggg atccaattga tgagattccc atcaattttt        49

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
gcccacgatg gagaaatcgc gagcttcagc ttctcttttc tc                42

<210> SEQ ID NO 17
<211> LENGTH: 42
<212> TYPE: DNA
<213> ORGANISM: Artificial Sequence
<220> FEATURE:
<223> OTHER INFORMATION: Primer

<400> SEQUENCE: 17 gaaaaagag aagctgaagc tcgcgatttc tccatcgtgg gc                 42

<210> SEQ ID NO 18
<211> LENGTH: 50
<212> TYPE: DNA
<213> ORGANISM: Artificial Sequence
<220> FEATURE:
<223> OTHER INFORMATION: Primer

<400> SEQUENCE: 18
actaattaca tgatgcggcc cactagttca tttcttctta gtaggataag        50

<210> SEQ ID NO 19
<211> LENGTH: 50

```
<212> TYPE: DNA
<213> ORGANISM: Artificial Sequence
<220> FEATURE:
<223> OTHER INFORMATION: Primer

<400> SEQUENCE: 19
gcaccgccag ccttgttgct gctctccccc gcgatttctc catcgtgggc        50

<210> SEQ ID NO 20
<211> LENGTH: 50
<212> TYPE: DNA
<213> ORGANISM: Artificial Sequence
<220> FEATURE:
<223> OTHER INFORMATION: Primer

<400> SEQUENCE: 20
taattacatg atgcggcccg cggccgctca tttcttctta gtaggataag        50

<210> SEQ ID NO 21
<211> LENGTH: 43
<212> TYPE: DNA
<213> ORGANISM: Artificial Sequence
<220> FEATURE:
<223> OTHER INFORMATION: Primer

<400> SEQUENCE: 21
acgacggtac ccggggatca agcttatggt caagttcgct tcc               43

<210> SEQ ID NO 22
<211> LENGTH: 43
<212> TYPE: DNA
<213> ORGANISM: Artificial Sequence
<220> FEATURE:
<223> OTHER INFORMATION: Primer

<400> SEQUENCE: 22
aactaattac atgatgcggc cctctagatt aagcataggt gtc               43

<210> SEQ ID NO 23
<211> LENGTH: 45
<212> TYPE: DNA
<213> ORGANISM: Artificial Sequence
<220> FEATURE:
<223> OTHER INFORMATION: Primer

<400> SEQUENCE: 23
cgttcctgaa cttgttgccc gggttggtgg cacttctgcc agcgc             45

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
gttcctgaac ttgttcggcg ggttggtggc ac                           32

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
gtgccaccaa cccgccgaac aagttcagga ac                           32
```

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
gttgctgctc tccccgttgg tggcacttc                                    29

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
gaagtgccac caacggggag agcagcaac                                    29

<210> SEQ ID NO 28
<211> LENGTH: 42
<212> TYPE: DNA
<213> ORGANISM: Artificial Sequence
<220> FEATURE:
<223> OTHER INFORMATION: Primer

<400> SEQUENCE: 28
tcctcaggag atccccaaca ttgttggtgg cacttctgcc ag                     42

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29
gttggggatc tcctgaggag cggggagagc agcaacaagg                        40

<210> SEQ ID NO 30
<211> LENGTH: 50
<212> TYPE: DNA
<213> ORGANISM: Artificial Sequence
<220> FEATURE:
<223> OTHER INFORMATION: Primer

<400> SEQUENCE: 30
aaacgacggt acccggggat caagcttatg gtttcttcgg cattcgcacc              50

<210> SEQ ID NO 31
<211> LENGTH: 50
<212> TYPE: DNA
<213> ORGANISM: Artificial Sequence
<220> FEATURE:
<223> OTHER INFORMATION: Primer

<400> SEQUENCE: 31
actaattaca tgatgcggcc ctctagacta ttccgacgga acaaagccgc              50

<210> SEQ ID NO 32
<211> LENGTH: 50
<212> TYPE: DNA
<213> ORGANISM: Artificial Sequence
<220> FEATURE:
<223> OTHER INFORMATION: Primer

```
<400> SEQUENCE: 32
ccgccagcct tgttgctgct ctcccccagc tacctatccc cgcacaaaac            50
```